United States Patent [19]

Tada

[11] Patent Number: 5,124,259
[45] Date of Patent: Jun. 23, 1992

[54] METHOD FOR ELECTROPORATION

[75] Inventor: Yuichi Tada, Mobara, Japan

[73] Assignee: Mitsui Toatsu Chemicals, Inc., Tokyo, Japan

[21] Appl. No.: 570,633

[22] Filed: Aug. 22, 1990

[30] Foreign Application Priority Data

Aug. 23, 1989 [JP] Japan .................................. 1-215050

[51] Int. Cl.$^5$ ........................ C12N 15/87; C12N 13/00
[52] U.S. Cl. .............................. 435/172.1; 435/173; 935/52
[58] Field of Search ................ 435/173, 172.1, 240.47, 435/240.1; 935/52, 56

[56] References Cited

FOREIGN PATENT DOCUMENTS 8602382 4/1986 PCT Int'l Appl. ................. 435/173

OTHER PUBLICATIONS

Zimmermann, et al., Effects of External Electric Fields on Cell Membranes Bioelectrochem & Bioenergetics vol. 3, pp. 58–83 1976.

Zhelev, et al. Correlation Between Physical Parameters in Electrofusion and Electroporation of Protoplasts Bioelectrochem & Bioenergetics vol. 20, pp. 155–167 1988.

Zerbib, et al. Electric Field Mediated Transformation: Isolation and Characterization of a TK+ Subclonk Biochem Biophys Res Comm. vol. 129, No. 3, pp. 611–618 1985.

Primary Examiner—John Doll
Assistant Examiner—George C. Elliott
Attorney, Agent, or Firm—Nixon & Vanderhye

[57] ABSTRACT

Disclosed is a method for electoporation with which higher transformation efficiency may be attained than that attained by the conventional methods. In the method of electroporation, cells and DNAs are suspended in a buffer containing potassium ion as a cation and an amino acid ion and/or an organic acid ion as an anion, and substantially not containing chloride ion, and high voltage is applied thereacross.

7 Claims, 1 Drawing Sheet

| CaMv35s-pro | β-gluduronidase | NOS-ter |

Fig. 1

| CaMv35s-pro | hygro. rst. | NOS-ter |

Fig. 2

METHOD FOR ELECTROPORATION

BACKGROUND OF THE INVENTION

I. Field of the Invention

This invention relates to a method for electroporation for introducing a gene, virus or an organelle into a cell.

II. Description of the Related Art

A method in which protoplasts and DNAs are suspended in a buffer and applying an electric voltage ("electro") across the suspension so as to form repairable small pores (poration) into the cell membrane of the protoplasts, thereby carrying out the introduction of the DNAs into the protoplast cells, is called electroporation. This method was developed recently and is becoming widely employed. In fact, transformants were obtained using this method in a number of plants such as tobacco and rice. In the conventional electroporation method, buffers containing a high concentration of chloride such as potassium chloride, sodium chloride, calcium chloride and magnesium chloride are often used (Fromm et al., Nature 319:791–793, (1986); Shimamoto et al., Nature 338:274–276 (1989); and Dekeser et al., Plant Physiol. 90:217–223 (1989)). Potassium ion is contained in plant cells at high concentration, and so the potassium ion contained in the buffer is thought to be required for compensating the potassium ion flowing out from the pores in the cell membrane. Further, calcium ion and magnesium ion are thought to contribute to the stabilization of the cell membrane, so that these ions in the buffer are assumed to be utilized for stabilization.

However, with the conventional electroporation process, the cells are more or less damaged, so that the frequency of the cell division of the cells is reduced. As a result, the efficiency of the transformation by the electroporation is not satisfactorily high.

One of the causes of the reduction in the cell division frequency is the damage of the cells directly given by the application of the high voltage. This drawback is thought to be inherent to the electroporation itself and may not be overcome. However, it is thought that this is not the only cause of the reduction in the cell division frequency. Thus, it is expected that the frequency of the cell division may be considerably increased by eliminating such other causes.

SUMMARY OF THE INVENTION

Accordingly, an object of the present invention is to provide a method for electroporation with which the frequency of the cell division of the protoplasts subjected to electroporation is higher than in the conventional electroporation methods, so as to attain high transformation efficiency.

The present inventor intensively studied to discover that in conventional electroporation, the chloride ion contained in the buffer in high concentration yields chlorine gas by the electrolysis caused by the high voltage applied to the suspension, and the thus formed chlorine gas damages the cells. Further, it was found by the present inventor that by the electrolysis, a portion of the suspension in the vicinity of the electrodes is made highly acidic and another portion of the suspension in the vicinity of the electrodes is made highly basic, and such a highly acidic or basic condition adversely affects the cells.

The present invention provides a method for electroporation comprising the steps of suspending cells to be transformed and DNAs to be introduced into said cells in a buffer containing potassium ion as a cation and an amino acid anion and/or an organic acid anion as an anion, and substantially devoid of chloride ion; and applying a voltage across said suspension.

As will be concretely shown in the Examples described below, in the method of the present invention, since the buffer used does not substantially contain chloride ion, so that chlorine gas is not generated by the electrolysis, the frequency of the cell division subjected to the electroporation is significantly higher than that attained in the conventional electroporation methods. Further, the degree of the expression of the DNA introduced into the cells is also increased. Still further, the efficiency of the transformation is also significantly increased. Thus, the method of the present invention enabled with certainty the introduction of DNAs into cells, especially into the plant cells, which previously was difficult to attain.

BRIEF DESCRIPTION OF THE DRAWINGS

FIG. 1 is a schematic illustration of plasmid pBI221 used for the evaluation of the transformation efficiency of electroporation; and FIG. 2 is a schematic illustration of a plasmid containing a hygromycin resistant gene, which is used for the evaluation of the degree of expression of the DNA introduced into the cells.

DETAILED DESCRIPTION OF THE PREFERRED EMBODIMENTS

The most characteristic feature of the method of the present invention resides in the composition of the buffer to be used. The buffer contains potassium ion which is necessary for the plant cells and preferably contains calcium ion and magnesium ion. In order to eliminate the generation of chlorine gas by the electrolysis, the buffer does not substantially contain (is virtually devoid of) chloride ion. In place of the chloride ion, one or more organic anions are contained in the buffer for paring with the cations contained in the buffer.

As mentioned above, the buffer to be used in the method of the present invention contains potassium ion. The concentration of potassium ion may preferably be 35–105 milligram equivalents/liter. If the concentration of potassium ion is outside this range, the efficiency of the transformation may be degraded.

The buffer to be used in the method of the present invention may preferably contain calcium ion and/or magnesium ion in addition to the potassium ion for further promoting the efficiency of the transformation. The concentration of calcium ion or magnesium ion may preferably be not more than 60 milligram equivalents/liter each. If the concentration of calcium ion or magnesium ion is higher than this range, the efficiency of the transformation may be degraded.

The buffer to be used in the method of the present invention contains at least one amino acid anion and/or an organic acid anion which pairs with the above-mentioned cations. As the amino acid anion, anions of acidic amino acids such as aspartic acid and glutamic acid are preferred. Preferred examples of the organic acid liberating the above-mentioned organic acid anion may include gluconic acid, malic acid, succinic acid, fumaric acid and maleic acid. The total concentration of the amino acid anions and the organic acid anions may preferably be 35–225 milligram equivalents/liter.

It is important that the buffer does not substantially contain chloride ion. If the chloride ion exists in the buffer, chlorine gas is generated by the electrolysis when the high voltage is applied across the cell suspension and so the cells are damaged, so that the transformation efficiency is degraded. The term "substantially does not contain chloride ion" means that the buffer does not contain chloride ion in the amount with which chlorine gas is generated in the quantity enough to damage the cells, when a voltage for carrying out the electroporation process is applied across the suspension. In a preferred mode, the buffer does not contain chloride ion at all.

Although the above-mentioned cations and anions may be independently incorporated in the buffer, it is preferred to dissolve salts formed between the above-mentioned cations and anions in the buffer because the preparation of the buffer is easy.

To prevent rapid change in pH of the buffer, the buffer may preferably also contain a buffering agent. Preferred examples of the buffering agent may include 2-(n-morpholino)ethanesulfonic acid (MES), bis(2-hydroxyethyl)iminotris(hydroxymethyl)methane, N-(2-acetamido)iminodiacetic acid, piperazine-N,N'-bis(2-ethanesulfonic acid), N-(2-acetamido)-2-aminoethanesulfonic acid and the like. The concentration of the buffering agent may preferably be 5-50 mM.

The buffer may preferably contain an osmoticum to prevent the disruption of the cells. Preferred examples of the osmoticum may include mannitol, sorbitol, glucose, sucrose and the like. The concentration of the osmoticum may preferably be about 0.25-0.7M.

The buffer may preferably have a pH of 3.0-7.0.

Each step of the electroporation method of the present invention will now be described.

In the buffer described above, protoplasts and DNAs to be introduced into the protoplast cells are suspended. The protoplasts may be isolated by known methods, for example, by the method of Fujimura et al (Plant Tissue Culture Lett. 2:74-75 (1985)). The population density of the cells may be, for example, $1 \times 10^5$ to $1 \times 10^7$ cells/ml and the concentration of the DNAs may be, for example, 1 to 100 μg/ml.

The thus prepared suspension is then placed in a electrode vessel for electroporation. The electrode vessel may be a conventional one. Then a high voltage pulse is applied across the suspension. The voltage and the time for applying the voltage may appropriately be selected depending on the diameter of the protoplasts. The shape of the electrodes and the conditions of the application of the voltage is not restricted and may be appropriately selected without undue experimentation. Usually, the voltage may be 100-1000 V/cm and the time for applying the voltage may be 0.1-50 msec.

After the application of the voltage, the protoplasts are collected by centrifugation and are cultured. The culture of the protoplasts may be accomplished by a known method which is suitable for the protoplasts employed. For example, rice protoplasts may be cultured by the method of Fujimura et al (supra).

After about 14 days from the beginning of the culture, the frequency of the cell division may be determined. Further, in the fifth week from the beginning of the culture, the number of small calli may be counted. By this, the effect of the electroporation on the cell division of the protoplasts subjected to the electroporation may be evaluated.

Whether or not the DNAs are introduced into the cells such that they can be expressed may be determined, for example, by the following method: That is, after two days from the beginning of the culture, protoplasts and cells derived therefrom are harvested and proteins are extracted therefrom. The amount of the product of the introduced DNA in the extracted proteins is then determined. For example, assuming that β-glucronidase gene originating from E. coli to which 35S promoter of cauliflower mosaic virus (CaMV) is ligated is employed as the DNA to be introduced into the cells. If this DNA is expressed in the cells, β-glucronidase which is not inherently contained in the plant cells is produced. The amount of this enzyme may be determined by carrying out the enzyme reaction employing 4-MUG which is a compound in which glucronic acid is attached to 4-methylumbelliferon (4-MU) as a substrate, and by measuring the fluorescence emitted from the reaction product 4-MU (Jefferson et al., The EMBO Journal 6:3901-3907).

Whether or not the DNA is stably inserted into the nuclei of the cells may be determined, for example, by the following method:

The hygromycin resistant gene (hygro.rst.) originating from E. coli to which the 35S promoter of cauliflower mosaic virus is used as the foreign DNA to be introduced into the cells. After 14 days' culture of the protoplasts subjected to the electroporation, hygromycin is added to the culture medium to a concentration of 50 μg/ml. In these conditions, the culture is continued for another three weeks and the number of grown calli is then counted. Since the cells which were not transformed are killed and only the transformed cells which express the inserted foreign DNA can survive, the transformation efficiency may easily be evaluated by counting the number of the survived calli (Hauptmann et al (Plant Physiol. 86:602-606).

The invention will now be described by way of examples thereof. It should be noted that the examples are presented for illustration purposes only and should not be interpreted in any restrictive way.

EXAMPLE 1

Protoplasts were isolated from a cultured cell suspension originating from a scutellum of rice (Oryza sativa cultivar (variety: Sasanishiki)) by the method of Fujimura et al (Plant Tissue Culture Lett. 2:74-75, 1985). The protoplasts were suspended in four different buffers with the compositions shown in Table 1, to a population density of $2 \times 10^6$ cells/ml. To each of the resulting solutions, a plasmid pBI221 having the structure shown in FIG. 1 was added to a concentration of 20 μg/ml. The plasmid pBI221 was prepared as described in Molecular Cloning, 86-94, Maniatis et al., Cold Spring Harbor Laboratory (1982). Further, for comparison, suspensions to which the plasmid was not added were also prepared.

The suspension was placed in a vessel for electroporation. The side walls of the vessel were a pair of stainless steel electrodes plated with gold sizing $2 \times 87.5$ mm, the distance therebetween being 4 mm. The vessel had an inner volume of 700 μl. Across the electrodes, a high attenuating voltage with an initial voltage of 475 V/cm having a time in which the voltage is attenuated to half of 30 msec was applied. Since the electroconductivity varies depending on the composition of the buffer used, the capacitance of the capacitor of the electric power source was changed within the range of 220–1100 μF so that the time constant is made constant.

After the discharge, protoplasts were collected by centrifugation and were cultured according to the method of Fujimura et al (supra). After 48 hours from the beginning of the culture, protoplasts were recovered and the amount of the expression of the GUS gene was determined by the method of Jefferson et al (The EMBO Journal 6:3901–3907, 1987). That is, the amount of the expression of the GUS gene was determined by determining the fluorescence from 4-MU which is a decomposition product of 4-MUG by β-glucronidase that is the product encoded by the GUS gene. The results are shown in Table 2.

As is apparent from Table 2, when the electroporation was performed on the rice protoplasts using buffer A or D which contained chloride ion, expression of the gene in the plasmid added to the suspension was not observed. In buffer D, the concentration of the buffering agent MES was increased so as to reduce the damage by the large pH change presented by the electrolysis when the high voltage is applied, but good results were not obtained. In contrast, with the buffer B or C, the fluorescence was increased, so that it was observed that the GUS gene was well expressed.

TABLE 1

Composition of Buffers

| Components (mM) | Buffer | | | |
|---|---|---|---|---|
| | A | B | C | D |
| Potassium Chloride | 70 | — | — | 70 |
| Potassium Aspartate | — | 70 | 35 | — |
| Potassium Glutamate | — | — | 35 | — |
| Calcium Chloride | 5 | — | — | 5 |
| Calcium Gluconate | — | 5 | 5 | — |
| Magnesium Aspartate | — | — | 5 | — |
| MES | 5 | 5 | 5 | 50 |
| Mannitol (unit: M) | 0.4 | 0.4 | 0.4 | 0.4 |
| pH | 5.8 | 5.8 | 5.8 | 5.8 |

TABLE 2

Amount (pg/hr) of Produced Fluorescent Substance (4-MU) of Samples Prepared by Electroporation Using Various Buffers

| Buffers | DNA(−) | DNA(+) | Difference |
|---|---|---|---|
| A | 221 | 174 | −47 |
| B | 142 | 184 | +42 |
| C | 141 | 200 | +59 |
| D | 203 | 184 | −19 |

EXAMPLE 2

Protoplasts originating from a scutellum of rice (*Oryza sativa cultivar* (variety: Norin 8) which were isolated from the method of Fujimura et al (supra) were suspended in the buffers shown in Table 1. To each of the suspensions, a plasmid having the structure shown in FIG. 2, which has a hygromycin resistant gene, was added to a concentration of 10 μg/ml. This plasmid was prepared as described in Molecular Cloning (supra). The suspensions were subjected to electroporation in the same manner as in Example 1, and the resulting cells were cultured by the method of Fujimura et al (supra). After 2 weeks from the beginning of the culture, 50 μg/ml of hygromycin was added and the culture was continued for another 3 weeks. The number of calli grown was counted. Further, as a control, the same operation was repeated except that hygromycin was not added. The results are shown in Table 3. In Table 3, the values are averages of three samples.

As is apparent from Table 3, a higher division frequency as well as more hygromycin resistant colonies were obtained when buffer B was used than in the case where buffer A was used.

TABLE 3

Divison Frequency and Number of Hygromycin-Resistant Colonies of Samples Subjected to Electroporation Using Different Buffers

| Buffer | Division Frequency (%) | Number of Resistant Colonies (per 1 petri dish) |
|---|---|---|
| A | 3.57 | 2.7 |
| B | 9.57 | 100.0 |

EXAMPLE 3

Protoplasts were isolated from a cultured cell suspension originating from a scutellum of rice (*Oryza sativa cultivar* (variety: Sasanishiki)) by the method of Fujimura et al (supra). To examine the influence of the potassium aspartate level on the degree of the gene expression, the protoplasts were suspended in the buffers shown in Table 4, and 20 μg/ml of plasmid pBI221 was added to each of the suspensions. The suspension was subjected to electroporation and to subsequent culturing in the same manner as in Example 1. After 48 hours from the beginning of the culture, protoplasts were collected and the degree of the GUS gene expression was determined by the method of Jefferson et al. The results are shown in Table 5.

TABLE 4

Composition of Buffers

| Components (mM) | Buffer | | | |
|---|---|---|---|---|
| | E | F | G | H |
| Potassium Aspartate | 0 | 35 | 70 | 105 |
| Calcium Gluconate | 5 | 5 | 5 | 5 |
| MES | 5 | 5 | 5 | 5 |
| Mannitol (unit: M) | 0.4 | 0.4 | 0.4 | 0.4 |
| pH | 5.8 | 5.8 | 5.8 | 5.8 |

TABLE 5

Amount (pg/hr) of Produced Fluorescent Substance (4-MU) of Samples Prepared by Electroporation Using Various Buffers

| Buffers | DNA(−) | DNA(+) | Difference |
|---|---|---|---|
| E | 154 | 140 | −14 |
| F | 162 | 166 | +4 |
| G | 166 | 188 | +22 |
| H | 176 | 203 | +27 |

EXAMPLE 4

Protoplasts were isolated from a cultured cell suspension originating from a scutellum of rice (*Oryza sativa cultivar* (variety: Sasanishiki)) by the method of Fujimura et al (supra). To examine the influence of the organic acid anion paring with potassium ion on the degree of the gene expression, the protoplasts were suspended in the buffers shown in Table 6, and 20 μg/ml of plasmid pBI221 was added to each of the suspensions. The suspension was subjected to electroporation and to subsequent culturing in the same manner as in Example 1. After 48 hours from the beginning of the culture, protoplasts were collected and the degree of the GUS gene expression was determined by the method of Jefferson et al. The results are shown in Table 7. It should be noted that since malic acid and succinic acid are dibasic acids, 35 mM each of these acids forms salts with 70 mM potassium ion.

It can be seen from Table 7 that stable transformation may be attained by employing an amino acid or an organic acid such as glutamic acid, malic acid and succinic acid.

TABLE 6

| Composition of Buffers | | | | |
|---|---|---|---|---|
| | Buffer | | | |
| Components (mM) | I | J | K | L |
| Potassium Aspartate | 70 | — | — | — |
| Potassium Glutamate | — | 70 | — | — |
| Potassium Malate | — | — | 35 | — |
| Potassium Succinate | — | — | — | 35 |
| Calcium Gluconate | 5 | 5 | 5 | 5 |
| MES | 5 | 5 | 5 | 50 |
| Mannitol (unit: M) | 0.4 | 0.4 | 0.4 | 0.4 |
| pH | 5.8 | 5.8 | 5.8 | 5.8 |

TABLE 7

Amount (pg/hr) of Produced Fluorescent Substance (4-MU) of Samples Prepared by Electroporation Using Various Buffers

| Buffers | DNA(−) | DNA(+) | Difference |
|---|---|---|---|
| I | 261 | 300 | +39 |
| J | 269 | 324 | +55 |
| K | 249 | 304 | +55 |
| L | 245 | 304 | +59 |

EXAMPLE 5

Protoplasts were isolated from a cultured cell suspension originating from a scutellum of rice (*Oryza sativa cultivar* (variety: Sasanishiki)) by the method of Fujimura et al (supra). To examine the influence of the concentration of potassium gluconate on the degree of the gene expression, the protoplasts were suspended in the buffers shown in Table 8, and 20 μg/ml of plasmid pBI221 was added to each of the suspensions. The suspension was subjected to electroporation and to subsequent culturing in the same manner as in Example 1. After 48 hours from the beginning of the culture, protoplasts were collected and the degree of the GUS gene expression was determined by the method of Jefferson et al. The results are shown in Table 9. In Table 9, the mark "X" indicates that the cell growth was scarcely observed, the mark "Δ" indicates that cell growth was not good and the mark "○" indicates that the cell growth was good.

As can be seen from Table 9, good cell growth was observed when the concentration of potassium ion was 35 to 105 milligram equivalents/liter. To attain this range of concentration of potassium ion, the concentration of the amino acid anion or the organic acid anion which pairs with the potassium ion is also required to be 35–105 milligram equivalents/liter.

TABLE 8

| Composition of Buffers | | | | | | |
|---|---|---|---|---|---|---|
| | Buffer | | | | | |
| Components (mM) | N | O | P | Q | R | S |
| Potassium Gluconate | 0 | 20 | 35 | 70 | 105 | 140 |
| MES | 5 | 5 | 5 | 5 | 5 | 5 |
| Mannitol (unit: M) | 0.4 | 0.4 | 0.4 | 0.4 | 0.4 | 0.4 |
| pH | 5.8 | 5.8 | 5.8 | 5.8 | 5.8 | 5.8 |

TABLE 9

Amount (pg/hr) of Produced Fluorescent Substance (4-MU) of Samples Prepared by Electroporation Using Various Buffers

| Buffers | DNA(−) | DNA(+) | Difference | Cell Growth |
|---|---|---|---|---|
| N | 160 | 143 | −17 | X |
| O | 161 | 155 | −6 | Δ |
| P | 168 | 177 | +9 | ○ |
| Q | 172 | 205 | +32 | ○ |
| R | 176 | 211 | +35 | ○ |
| S | 178 | 193 | +15 | Δ |

EXAMPLE 6

Protoplasts were isolated from a cultured cell suspension originating from a scutellum of rice (*Oryza sativa cultivar* (variety: Sasanishiki)) by the method of Fujimura et al (supra). To examine the influence of the concentration of calcium gluconate and calcium aspartate on the degree of the gene expression, the protoplasts were suspended in the buffers shown in Table 10, and 20 μg/ml of plasmid pBI221 was added to each of the suspensions. The suspension was subjected to electroporation and to subsequent culturing in the same manner as in Example 1. After 48 hours from the beginning of the culture, protoplasts were collected and the degree of the GUS gene expression was determined by the method of Jefferson et al. The results are shown in Table 11. In Table 11, the mark "X" indicates that the cell growth was scarcely observed, the mark "Δ" indicates that cell growth was not good and the mark "○" indicates that the cell growth was good.

As can be seen from Table 11, more efficient transformation can be attained by adding a calcium salt such as calcium gluconate or calcium aspartate to a concentration of 5–30 mM, i.e., 10–60 milligram equivalents/liter in addition to potassium aspartate.

TABLE 10

| Composition of Buffers | | | | | | |
|---|---|---|---|---|---|---|
| | Buffer | | | | | |
| Components (mM) | T | U | V | W | X | Y |
| Potassium Aspartate | 70 | 70 | 70 | 70 | 70 | 70 |
| Calcium Gluconate | 0 | 5 | 30 | 50 | 0 | 0 |
| Calcium Aspartate | 0 | 0 | 0 | 0 | 5 | 30 |
| MES | 5 | 5 | 5 | 5 | 5 | 5 |
| Mannitol (unit: M) | 0.4 | 0.4 | 0.4 | 0.4 | 0.4 | 0.4 |
| pH | 5.8 | 5.8 | 5.8 | 5.8 | 5.8 | 5.8 |

TABLE 11

Amount (pg/hr) of Produced Fluorescent Substance (4-MU) of Samples Prepared by Electroporation Using Various Buffers

| Buffers | DNA(−) | DNA(+) | Difference | Cell Growth |
|---|---|---|---|---|
| T | 199 | 233 | +34 | ○ |
| U | 182 | 245 | +63 | ○ |
| V | 184 | 241 | +57 | ○ |
| W | 189 | 231 | +42 | Δ |
| X | 176 | 241 | +65 | ○ |
| Y | 178 | 237 | +59 | ○ |

EXAMPLE 7

Protoplasts were isolated from a cultured cell suspension originating from a scutellum of rice (*Oryza sativa cultivar* (variety: Sasanishiki)) by the method of Fujimura et al (supra). To examine the influence of the concentration of magnesium aspartate on the degree of the gene expression, the protoplasts were suspended in the buffers shown in Table 12, and 20 μg/ml of plasmid pBI221 was added to each of the suspensions. The suspension was subjected to electroporation and to subsequent culturing in the same manner as in Example 1. After 48 hours from the beginning of the culture, protoplasts were collected and the degree of the GUS gene expression was determined by the method of Jefferson et al. The results are shown in Table 13. In Table 13, the mark "X" indicates that the cell growth was scarcely observed, the mark "Δ" indicates that cell growth was not good and the mark "○" indicates that the cell growth was good.

As can be seen from Table 13, more efficient transformation can be attained by adding a magnesium salt such as magnesium aspartate to a concentration of 5-30 mM, i.e., 10-60 milligram equivalents/liter in addition to potassium aspartate. By further adding 5-30 mM calcium gluconate, still more efficient transformation can be attained.

TABLE 12

| | Composition of Buffers | | | | | |
| --- | --- | --- | --- | --- | --- | --- |
| | | | Buffer | | | |
| Components (mM) | Z | a | b | c | d | e |
| Potassium Aspartate | 105 | 105 | 105 | 105 | 105 | 105 |
| Magnesium Aspartate | 0 | 5 | 30 | 50 | 30 | 30 |
| Calcium Gluconate | 0 | 0 | 0 | 0 | 5 | 30 |
| MES | 5 | 5 | 5 | 5 | 5 | 5 |
| Mannitol (unit: M) | 0.4 | 0.4 | 0.4 | 0.4 | 0.4 | 0.4 |
| pH | 5.8 | 5.8 | 5.8 | 5.8 | 5.8 | 5.8 |

TABLE 13

Amount (pg/hr) of Produced Fluorescent Substance (4-MU) of Samples Prepared by Electroporation Using Various Buffers

| Buffers | DNA(−) | DNA(+) | Difference | Cell Growth |
| --- | --- | --- | --- | --- |
| Z | 185 | 198 | +13 | ○ |
| a | 165 | 205 | +40 | ○ |
| b | 161 | 201 | +40 | ○ |
| c | 171 | 190 | +19 | X |
| d | 157 | 208 | +51 | ○ |

TABLE 13-continued

Amount (pg/hr) of Produced Fluorescent Substance (4-MU) of Samples Prepared by Electroporation Using Various Buffers

| Buffers | DNA(−) | DNA(+) | Difference | Cell Growth |
| --- | --- | --- | --- | --- |
| e | 159 | 206 | +47 | ○ |

Although the invention was described by way of preferred examples thereof, it is apparent for those skilled in the art that various modifications may be made without departing from the spirit and scope of the present invention.

We claim:

1. A method for electroporation comprising the steps of:
   (a) suspending cells to be transformed and DNAs to be introduced into said cells in a buffer containing potassium ion as a cation and an amino acid anion, an organic acid anion or both an amino acid and an organic acid as an anion to pair with the cation, wherein the concentration of said potassium ion in said buffer being 35-105 milligram equivalents/liter, said buffer being substantially or completely devoid of chloride ion; and
   (b) applying a voltage across said suspension.

2. The method of claim 1, wherein said buffer further contains calcium ion with a concentration of not more than 60 milligram equivalents/liter.

3. The method of claim 1, wherein said buffer further contains magnesium ion with a concentration of not more than 60 milligram equivalents/liter.

4. The method of claim 1, wherein said buffer further contains calcium ion with a concentration of not more than 60 milligram equivalents/liter and magnesium ion with a concentration of not more than 60 milligram equivalents/liter.

5. The method of claim 1, wherein said amino acid is aspartic acid or glutamic acid.

6. The method of claim 1, wherein said organic acid is gluconic acid, malic acid, succinic acid, fumaric acid or maleic acid.

7. The method of claim 1, wherein the total concentration of said anion in said buffer is 35-225 milligram equivalents/liter.

* * * * *